United States Patent [19]

Schmidlin et al.

[11] 3,993,644

[45] Nov. 23, 1976

[54] PROCESS FOR THE MANUFACTURE OF 11β,18-OXIDO-18,21-DIHYDROXY-20-OXO-PREGNANE COMPOUNDS

[75] Inventors: Julius Schmidlin; Michel Biollaz, both of Basel, Switzerland

[73] Assignee: Ciba-Geigy Corporation, Ardsley, N.Y.

[22] Filed: Jan. 20, 1975

[21] Appl. No.: 542,148

[30] Foreign Application Priority Data

Jan. 28, 1974  Switzerland............................ 1104/74
Feb. 25, 1974  Switzerland............................ 2628/74

[52] U.S. Cl............... 260/239.55 R; 260/239.55 C; 260/239.57
[51] Int. Cl.$^2$........................................ C07J 17/00
[58] Field of Search............................ 260/239.55; /Machine Searched Steroids

[56] References Cited
UNITED STATES PATENTS

| | | | |
|---|---|---|---|
| 3,135,773 | 6/1964 | Wettstein et al............... | 260/397.45 |
| 3,178,414 | 4/1965 | Meystre et al.................. | 260/239.55 |
| 3,264,289 | 8/1966 | Schmidlin...................... | 260/239.55 |

*Primary Examiner*—Elbert L. Roberts
*Attorney, Agent, or Firm*—Joseph G. Kolodny; John J. Maitner; Theodore O. Groeger

[57] ABSTRACT

A new method for converting 11β,18; 18,20-bis-epoxy-pregn-20-enes to 11β,18-epoxy-18,21-dihydroxy-20-oxo-pregnane compounds or functional derivatives thereof is described and claimed. It consists in treating said bis-epoxy compounds with a heavy metal acylate having an acyloxylating action, such as lead - (IV), cerium - (IV), mercury - (II) and thallium - (III) - acylates. Preferred agent is lead tetraacetate. The reaction is conducted in a solvent or suspending agent like benzene or its homologs or chlorinated paraffins, like methylene chloride, preferably at room temperature and optionally in the presence of an acid.

In the 21- acylates of 11β,18-epoxy-18,21-dihydroxy-20-oxo-pregnane compounds thus obtained the 21-hydroxy group and any other protected functional groups can be set free in manner known.

The process is especially important for the manufacture of aldosterone or its derivatives.

15 Claims, No Drawings

PROCESS FOR THE MANUFACTURE OF 11β, 18-OXIDO-18,21-DIHYDROXY-20-OXO-PREGNANE COMPOUNDS

The present invention relates to a new process for the manufacture of 11β, 18-epoxy-18,21-dihydroxy-20-oxo-pregnane compounds or functional derivatives thereof, particularly 21-esters thereof. This class of compounds includes known steroids which have a pharmacological action, such as, in particular, aldosterone and derivatives thereof.

Among the various syntheses of aldosterone and its derivatives which have been described, syntheses of special importance are particularly those which start from the lactone of the formula

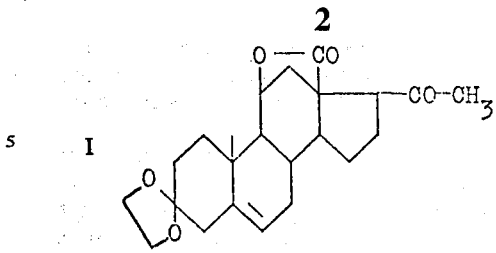

because this compound can be prepared relatively easily from 11α-hydroxyprogesterone, which is obtainable in industrial quantities. Among these syntheses, the synthesis which is particularly suitable for the industrial preparation of aldosterone is, in turn, the synthesis which leads to the end product via the 20,21-enol ether of the formula IV and the secondary products V–VII, in accordance with the following equation:

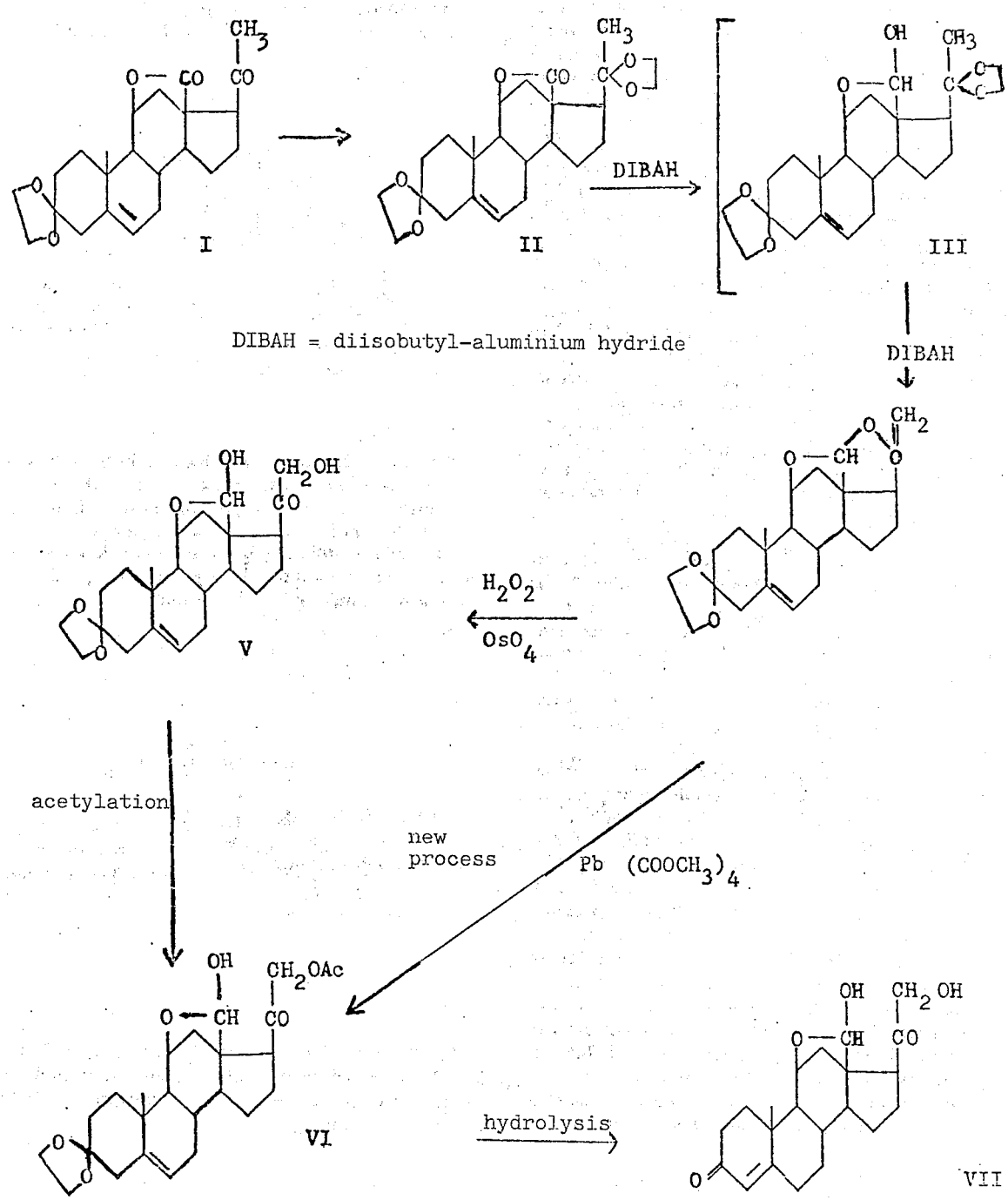

DIBAH = diisobutyl-aluminium hydride

This process is described, for example, in British Patent No. 1,080,327, the compounds of the formula III of the above equation figuring there as the starting materials. It is a particular advantage of this process that the starting materials III mentioned can be prepared in situ by using the same reagent (for example diisobutyl-aluminium hydride) which is also used in the further stage III–IV, so that the sequence of stages II–IV can be carried out as a one-pot process. The conversion of the 20,21-enol ether IV into the aldosterone-3-ketal V is carried out, according to the process of the British Patent mentioned, by treatment with hydroxylating agents, such as osmium tetroxide, ruthenium tetroxide or manganese dioxide, tungsten trioxide or vanadium pentoxide, or using epoxidising agents, such as organic per-acids and subsequent hydrolysis or acylolysis.

It has now been found, in accordance with the present invention, that IV can be converted, by treatment with heavy metal salts of the type of lead tetraacetate which have an acyloxylating action, into the 3-ethylene ketal VI directly and in a good yield, which produces a further advance in the industrial preparation of aldosterone and derivatives thereof. The use of heavy metal salts which have an acyloxylating action, especially lead tetraacetate, instead of the expensive, volatile and toxic osmium tetroxide, is a great advantage in both a general technical respect and in regard to ecology. Furthermore, the working up of the reaction products is very easy and convenient, since no mixtures are formed which are difficult to separate. A smooth conversion of IV into the 21-acylaldosterone ketal VI in accordance with the present process is surprising, in view of the variety of ways in which the oxidising agents involved can react with substrates of this kind.

The process according to the invention is, therefore, characterised in that a heavy metal acylate which has an acyloxylating action is allowed to act upon an 11α,18;18,20-bis-epoxy-pregn-20-ene compound in an inert solvent or suspending agent, with the optional addition of an acid or a base, and, if desired, the 21-acyloxy group in the 21-acyloxy-18-hydroxy-11β,18-epoxy-20-oxo-pregnane compound thus obtained is converted into the free hydroxyl group and/or optionally functionally modified groups are converted into the free groups, and/or functional groups are functionally modified.

The pregnene compounds which are to be used as the starting materials can be substituted in any desired way in the steroid skeleton and/or can contain one or more double bonds. Examples of substituents which can be present are functional groups, especially hydroxyl and/or oxo groups, preferably in a protected form, that is to say in a functionally modified form. 11β,18;18,20-Bis-epoxy-pregn-20-ene compounds which are unsubstituted in the 18- and 21-position are preferably used as the starting materials and, among these, especially those which are unsubstituted in the 17-position.

A functionally modified hydroxyl group is particularly an esterified or etherified hydroxyl group, and a functionally modified oxo group is particularly a ketalised oxo group. Among the esters, preferred esters are those which are derived from carboxylic acids having 1–18 C atoms, for example from aliphatic, aromatic, araliphatic or heterocyclic acids, and, particularly, from lower aliphatic carboxylic acids having 1–7 C atoms, such as acetic acid, propionic acid, the butyric acids, the valeric acids or the caproic acids. Among the ester groups which are derived from aromatic acids, the benzoates should be mentioned especially. Among the ether groups, those ether groups should be particularly singled out which are derived from lower aliphatic alkanols having 1–7 C atoms, or from monocyclic aryl-lower aliphatic alcohols, such as the phenyl-lower alkyl alcohols, for example benzyl alcohol or phenethyl alcohol, or from heterocyclic alcohols of the tetrahydrofuranol or tetrahydropyranol type, or from tri-lower alkyl silanols. Starting materials which are particularly selected are those which have a protected hydroxyl or oxo group in the 3-position, which group can be converted, after the treatment with the heavy metal acylate having an acyloxylating action and, if desired, after liberating the hydroxyl group in the 21-position, into the free hydroxyl or oxo group.

Preferred starting materials are those of the formula

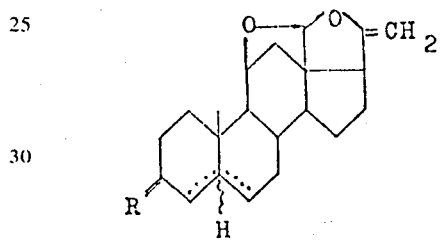

(A)

in which the 5H atom can be located in the α-position or the β-position, and the broken lines in the 4,5- and 5,6-position designate a possible double bond, and wherein R denotes, conjointly with hydrogen, a free or functionally modified hydroxyl group or denotes a free or functionally modified oxo group, and particularly the known compound of the formula

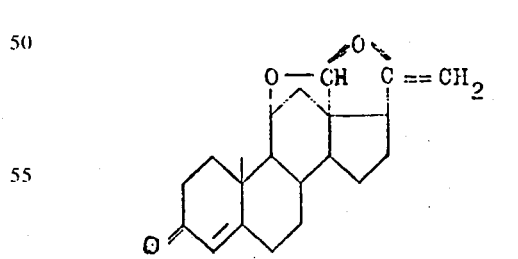

(B)

and particularly 3-ketals thereof, above all the 3-ethylene ketal, which lead to aldosterone esters or ketals thereof through the application of the process of the present invention.

Examples of possible heavy metal acylates which have an acyloxylating action are lead-(IV) acylates, mercury-(II) acylates cerium-(IV) acylates and thallium-(III) acylates. Particular use is made of the acylates of lower aliphatic carboxylic acids having 1–7 C atoms, such as the acetates, propionates, butyrates, valerates or caproates or, especially, also the trihalogenoacetates, such as trifluoroacetates, or acylates of monocyclic aromatic carboxylic acids, such as benzoic acid or homologues. Lead tetraacetate is a preferred reagent.

The reaction of the starting materials mentioned with the above-mentioned agents is carried out in an inert solvent or suspending agent, with the optional addition of an acid or a base.

A Bronstedt or Lewis acid or mixtures thereof are used as the acids; preferably the same carboxylic acid is used which corresponds to the acid radical of the acylate used, that is to say, for example, acetic acid, if the reaction is carried out using lead tetraacetate. Tertiary nitrogen bases of an aromatic character, such as, for example, pyridine, collidine or morpholine are preferably used as the bases. In many cases, even weaker bases are adequate, such as some of the solvents mentioned below, for example ethers, such as dioxane or tetrahydrofurane.

Examples of suitable inert solvents are aliphatic or aromatic or cycloaliphatic hydrocarbons or their halogenated, especially chlorinated, derivatives, such as, for example, the higher liquid paraffins, chlorinated paraffins, such as methylene chloride, ethylene chloride or chloroform, cyclohexane and its homologues, benzene and its homologues, chlorobenzene and chlorotoluenes, ethers, such as the lower aliphatic ethers, dioxane, tetrahydrofurane, and also bifunctional ethers, such as alkylene glycol dialkyl ethers, for example ethylene glycol dimethyl ether or ethylene glycol diethyl ether, esters, such as those of lower aliphatic acids and lower aliphatic, monohydric or dihydric alcohols, for example ethyl acetate, butyl acetate, amyl acetate or ethylene glycol diacetate, amides, such as dialkylacylamides of lower aliphatic acids, for example dialkylformamides, such as dimethylformamide or diethylformamide, or ketones, such as the lower aliphatic ketones, for example acetone or methyl ethyl ketone or the customary cycloaliphatic ketones which are used as solvents, such as cyclopentanone or cyclohexanone.

The reaction is advantageously carried out at room temperature or at a lower temperature for example down to −20°. It can, however, also be carried out at an elevated temperature, for example up to approx. 100°. The reaction time is from a few minutes to several hours, depending on the starting material.

Working up is carried out in a manner which is in itself known: after the reaction is complete, the mixture is, for example, filtered to remove reduced oxidising agent, the organic solution is washed with water or aqueous salt solutions, and/or, in order to neutralise any acids present, is optionally washed with bases, the solvent is evaporated and the oxidation product is isolated in a customary manner, for example by chromatography or crystallisation, from the residue.

If the reaction mixture is worked up in a gentle manner, avoiding alkaline conditions, the desired 21-hydroxylated process products, for example aldosterone, are generally obtained in the form of the 21-acylates. The 21-hydroxyl group can be formed from the 21-acylates in a manner which is in itself known, for example by alkaline saponification. The liberation, which is optionally to be carried out, of functionally modified groups or the modification of functional groups, for example the acylation of a 21-hydroxyl group, in the steroid skeleton is likewise carried out in a manner which is in itself known; thus ketal groups present, for example in the 3-position, are split by acid hydrolysis, for example using dilute acids, particularly using 50–90% strength aqueous acetic acid. Ether groups are also split by means of acids in a manner which is in itself known and ester groups are split by means of acids or, optionally, by means of bases.

A particularly important embodiment of the present process consists of starting from 3-ketals, particularly 3-ethylene ketals, of the compounds of the above formula B, allowing the acyloxylating heavy metal salt, preferably lead tetraacetate, to act upon these and, before or after liberating the 21-hydroxyl group, splitting the ketal group with the formation of 21-acylaldosterone or aldosterone.

The starting materials are known or can be prepared by methods which are in themselves known.

The invention also relates to those embodiments of the process in which compounds obtainable as an intermediate product at any stage are used as starting materials and the missing steps are carried out, or the process is discontinued at any desired stage, or in which a starting material is formed under the reaction conditions or is used in the form of a salt.

The following examples illustrate the invention without, however, limiting it in any respect.

EXAMPLE 1

520 mg of lead tetraacetate (containing 10–15% of free acetic acid) are dissolved in 10 ml of absolute benzene to which 1 ml of glacial acetic acid has been added, and 200 mg of 3,3-ethylenedioxy-11$\beta$,18;18,20-bis-epoxypregna-5,20-diene (melting point 212°–216° C) are added with stirring at room temperature, a clear solution being formed. A white precipitate is deposited after a few minutes. After approx. 10 minutes, the mixture is poured onto ice, the whole is extracted with ethyl acetate, and the organic phase is separated off and washed 3 times each with saturated sodium chloride solution and then with water. After separating off the aqueous phase, the organic extract is dried over sodium sulphate and evaporated in vacuo and the residue is heated with 90 percent strength aqueous acetic acid. 11$\beta$,18-Epoxy-18,21-dihydroxypregn-4-ene-3,20-dione-21-acetate (21-0-acetyl-aldosterone) of melting point 184°–188.5° C is isolated from the reaction mixture in a known manner and can be converted into aldosterone in a manner which is also known.

EXAMPLE 2

500 mg of lead tetraacetate are added to an anhydrous solution of 185 mg of 3,3-ethylenedioxy-11$\beta$,18;18,20-bis-epoxypregna-5,20-diene in 10 ml of benzene in an atmosphere of dry nitrogen, subsequently rinsing with 1 ml of 100 percent strength acetic acid. After stirring for 4 hours at room temperature, the reaction solution is decanted from the lead diacetate which has separated out, excess lead tetraacetate is decomposed by shaking with aqueous 0.1 molar oxalic acid solution, after dilution with benzene and much ether, the organic phase is washed further with water, dried using sodium sulphate and evaporated. The nearly colourless, crystalline residue is pure 3,3-ethylenedioxy-11$\beta$,18-epoxy-18,21-dihydroxy-pregn-5-en- 20-one-21-acetate, which is subjected to the ketal splitting reaction without further purification.

235 mg of crude 3,3-ethylenedioxy-11β,18-epoxy-18,21-dihydroxy-pregn-5-en-20-one-21-acetate in 5 ml of 90 percent strength aqueous acetic acid are heated to 97°–100° C for 10 minutes. The solution is then cooled to approx. 25° C and the reaction solution is evaporated in vacuo while adding toluene. The acid-free residue is dissolved in chloroform and is separated by the continuous flow method over 12.5 g of silica gel (containing 10% of water) using chloroform-acetone mixtures with an increasing acetone content. 11β,18-Epoxy-18,21-dihydroxy-pregn-4-ene-3,20-dione-21-acetate (21-0-acetyl-aldosterone) of melting point 195°–198° C is obtained by recrystallising from acetone the middle fractions which are virtually homogeneous according to thin layer chromatography.

EXAMPLE 3

370.5 mg of 3,3-ethylenedioxy-11β,18;18,20-bis-epoxypregna-5,20-diene are initially taken in an atmosphere of dry nitrogen and are dissolved in 5 ml of anhydrous methylene chloride, with exclusion of moisture, and 560 mg of lead tetraacetate, free from acetic acid, are then added, with rapid stirring. A milky cloudiness is immediately formed, which is transformed after a few minutes into a nearly colourless, crystalline deposit. After stirring for 35 minutes, the reaction material is poured onto an aqueous solution which is 0.1 molar in respect of sodium thiosulphate and in respect of sodium iodide, and ice, and the mixture is extracted with ethyl acetate. The extracts are washed with 1 molar ammonium bicarbonate and water and are combined, dried by means of sodium sulphate, filtered and evaporated. The residual crude oxidation product, 3,3-ethylenedioxy-11β,18-epoxy-18,21-dihydroxy-pregn-5-en-20-one-21-acetate, crystallises completely from ether and is subjected to the ketal splitting reaction without further purification.

7.5 ml of 67 percent strength aqueous acetic acid are poured over the crude oxidation product (495 mg) obtained in accordance with the above instructions, and the mixture is first heated for 1 hour, with stirring, in a bath at 62°–65° C. While continuing the stirring, the reaction solution is then diluted at 62°–65° C and over the course of 1½ hours with 17.5 ml of water and is then cooled to 12°–15° C. The crude hydrolysis product which crystallises out in the course thereof weighs 315 mg after drying. 267 mg of pure 11β,18-epoxy-18,21-dihydroxy-pregn-4-ene-3,20-dione-21-acetate (21-0-acetyl-aldosterone) of melting point 195°–198° C are obtained by column chromatography over 30 g of silica gel (containing 10% of water), elution with methylene chloride-acetone mixtures of increasing acetone content, and recrystallisation from methylene chloride-ether of the fractions which are homogeneous according to thin layer chromatography.

Extractive working up of the aqueous mother liquor from the ketal splitting reaction described above gives a further quantity of crystalline hydrolysis product, which, together with the as yet impure fractions from the above chromatogram, gives further quantities of pure 11β,18-epoxy-18,21-dihydroxy-pregn-4-ene-3,20-dione-21-acetate (21-0-acetyl-aldosterone) of melting point 195°–198° C, after further separation by column chromatography over silica gel, using toluene-chloroform mixtures.

We claim:

1. Process for the manufacture of 21-acylates of 11β,18-epoxy-18,21-dihydroxy-20-oxo-pregnane compounds wherein a lead tetraacylate which has an acyloxylating action is allowed to act upon an 11β,18;18,20-bis-epoxy-pregn-20-ene compound in an inert solvent.
2. Process according to claim 1, wherein an 11β,18;18,20-bis-epoxy-pregn-20-ene compound which is unsubstituted in the 17,18 and 21-position is used as the starting material.
3. Process according to claim 1, characterised in that a compound of the formula

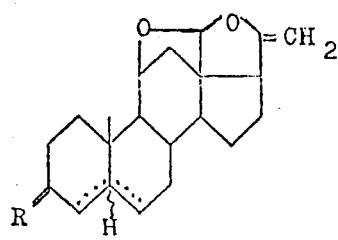

(A)

in which the 5H atom can be located in the α-or β-position, and the broken lines in the 4,5- and 5,6-position designate a possible double bond and where R denotes a member selected from the group consisting of a hydrogen atom together with a free, esterified or etherified hydroxyl group and a free or ketalised oxo group, is used as starting material.

4. Process according to claim 1, characterised in that a compound of the formula

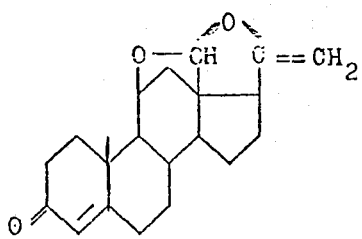

(B)

or the corresponding Δ⁵-3,3-ethylenedioxy compounds is used as the starting material.

5. Process as claimed in claim 1, wherein acylates of lower aliphatic carboxylic acids having 1–7 C atoms are used.
6. Process as claimed in claim 5, wherein lead tetraacetate is used.
7. Process as claimed in claim 1, wherein the treatment of the starting materials with the metal acylate is carried out in a member selected from the group consisting of an aromatic hydrocarbon, a halogenated lower aliphatic hydrocarbon, an open chain or cyclic aliphatic ether and a lower aliphatic ester.
8. Process as claimed in claim 7, wherein a member selected from the group consisting of benzene and its homologs and methylene chloride is used as the solvent.
9. Process as claimed in claim 1, wherein the reaction is carried out in the presence of a member selected from the group consisting of a Bronstedt acid and a Lewis acid.

10. Process as claimed in claim 9, wherein there is used the carboxylic acid corresponding to the lead tetraacylate used.

11. Process as claimed in claim 1, wherein the reaction is carried out within the temperature range between room temperature and approximately −20°.

12. Process as claimed in claim 1, wherein in the obtained 21-acylates the 21-acyloxy group is saponified with an alkaline agent to obtain the 11β,18-epoxy-18,21-dihydroxy-20-oxo-pregnane compounds.

13. Process as claimed in claim 1, wherein in the obtained 21-acylates of 11β,18-epoxy-18,21-dihydroxy-20-oxo-pregnane compounds any protected hydroxy or oxo group present in 3-position is liberated by acid treatment.

14. Process according to claim 1 wherein the reaction is carried out in the presence of a base or an acid.

15. Process according to claim 1, wherein the reaction is carried out in the presence of a tertiary nitrogen base of aromatic character.

* * * * *